US010878958B2

(12) United States Patent
Mukumoto et al.

(10) Patent No.: US 10,878,958 B2
(45) Date of Patent: Dec. 29, 2020

(54) INFORMATION INTEGRATING APPARATUS

(71) Applicants: TOKYO WOMEN'S MEDICAL UNIVERSITY, Tokyo (JP); OPExPARK Inc., Tokyo (JP)

(72) Inventors: Go Mukumoto, Kariya (JP); Hideki Okuda, Kariya (JP); Jun Okamoto, Tokyo (JP); Yoshihiro Muragaki, Tokyo (JP)

(73) Assignees: TOKYO WOMEN'S MEDICAL UNIVERSITY, Tokyo (JP); OPExPARK Inc., Tokyo (JP)

( * ) Notice: Subject to any disclaimer, the term of this patent is extended or adjusted under 35 U.S.C. 154(b) by 0 days.

(21) Appl. No.: 16/419,344

(22) Filed: May 22, 2019

(65) Prior Publication Data

US 2019/0272918 A1 Sep. 5, 2019

Related U.S. Application Data

(63) Continuation of application No. PCT/JP2017/042900, filed on Nov. 29, 2017.

(30) Foreign Application Priority Data

Dec. 7, 2016 (JP) ................................. 2016-237730

(51) Int. Cl.
*G16H 40/63* (2018.01)
*G16H 20/40* (2018.01)
(Continued)

(52) U.S. Cl.
CPC ............... *G16H 40/63* (2018.01); *A61B 5/00* (2013.01); *A61B 34/20* (2016.02); *G06F 3/14* (2013.01); *G16H 20/40* (2018.01)

(58) Field of Classification Search
CPC ........ G16H 40/60; G16H 40/63; A61B 34/20; A61B 34/25; A61B 2034/252;
(Continued)

(56) References Cited

U.S. PATENT DOCUMENTS 9,788,907 B1* 10/2017 Alvi ........................ G16H 70/20
10,073,515 B2* 9/2018 Awdeh ..................... G06F 3/012
(Continued)

FOREIGN PATENT DOCUMENTS

JP 2003339735 A 12/2003
JP 2004008582 A 1/2004
(Continued)

*Primary Examiner* — Emily C Terrell
(74) *Attorney, Agent, or Firm* — Harness, Dickey & Pierce, P.L.C.

(57) ABSTRACT

One embodiment of the present disclosure is provided with: an information acquisition portion; an information storage portion; an event extraction section; a region setting section; and a display section. The information storage portion adds, to medical information, a time at which the information acquisition portion acquires the medical information from each of multiple medical devices used in a surgery, and a label for specifying the medical information. The display section causes a display device to display, as medical information, an image including a surgery site and at least one event extracted by the event extraction section in a time region set by the region setting section based on the time added to the medical information.

7 Claims, 6 Drawing Sheets

(51) Int. Cl.
*G06F 3/14* (2006.01)
*A61B 5/00* (2006.01)
*A61B 34/20* (2016.01)

(58) Field of Classification Search
CPC ........ A61B 2034/254; A61B 2034/256; A61B 2034/258; G06F 3/14
USPC .................................................... 340/870.4
See application file for complete search history.

(56) References Cited

U.S. PATENT DOCUMENTS

| | | | |
|---|---|---|---|
| 2004/0138548 A1* | 7/2004 | Strommer | A61B 5/0555 600/407 |
| 2007/0136218 A1* | 6/2007 | Bauer | G06F 19/3481 706/12 |
| 2008/0319275 A1* | 12/2008 | Chiu | A61B 5/7289 600/300 |
| 2015/0278178 A1 | 10/2015 | Okuda et al. | |
| 2018/0168737 A1* | 6/2018 | Ren | A61B 3/0058 |

FOREIGN PATENT DOCUMENTS

| | | | |
|---|---|---|---|
| JP | 2006136441 A | 6/2006 | |
| JP | 2015185125 A | 10/2015 | |

* cited by examiner

INFORMATION INTEGRATING APPARATUS

CROSS REFERENCE TO RELATED APPLICATIONS

The present application is a continuation application of International Patent Application No. PCT/JP2017/042900 filed on Nov. 29, 2017, which designated the United States and claims the benefit of priority from Japanese Patent Application No. 2016-237730 filed on Dec. 7, 2016. The entire disclosures of all of the above application are incorporated herein by reference.

TECHNICAL FIELD

The present disclosure relates to a technique for displaying medical information acquired from a medical device used in a surgery.

BACKGROUND

There has been known a technique for acquiring medical information from multiple medical devices used in a surgery, integrating multiple pieces of the medical information, and displaying the integrated medical information on a display device.

SUMMARY

The present disclosure according to one aspect provides an information integrating apparatus that is configured to: acquire medical information; store the medical information; extract an event to be displayed; set a time region for displaying the event; and display an image including a surgical site and the event.

BRIEF DESCRIPTION OF DRAWINGS

The above and other objects, features, and advantages of the present disclosure will become more apparent from the following detailed description with reference to the accompanying drawings. In the drawings.

DETAILED DESCRIPTION

The inventors of the present application have found the followings.

A related art describes a technique for applying a time tag that indicates the time when medical information is acquired and a type tag that indicates the type of medical information to medical information acquired and storing the medical information. A related art also describes a technique for setting a time region from a start point to an end point and displaying medical information with a time tag indicating the time that falls within the set time region on a display device as images, graphs, tables, and the like.

A related art describes a technique for reading a time tag when a condition that, for example, specific biological information changes suddenly is satisfied and setting a time region in which the time indicated by the time tag read is the start point, the end point, or the center. A related art also describes a technique for displaying medical information with a time tag that falls within the set time region on the display device.

A technique of a related art may have a difficulty that medical information with a time tag that falls within a set time region is displayed on a display device, but it is not assumed to extract medical information to be paid attention to in the time region and to display the medical information.

According to an aspect of the present disclosure, it may be preferable to provide a technique for extracting medical information to be paid attention to in a time region and displaying the medical information.

According to one aspect of the present disclosure, an information integrating apparatus may include an information acquisition portion, an information storage portion, an event extraction section, a region setting section, and a display section.

The information acquisition portion acquires medical information from each of multiple medical devices used in a surgery. The information storage portion manages a time when the information acquisition portion acquires the medical information on a time axis unified and applies the time to the medical information, applies a label for specifying the medical information to the medical information, and stores the medical information in a storage device. The event extraction section extracts at least one event to be displayed on a display device from the medical information stored in the storage device based on the label applied to the medical information.

The region setting section sets a time region for displaying the at least one event extracted by the event extraction section on the display device. The display section displays, as the medical information, an image including a surgical site and the at least one event extracted by the event extraction section in the time region set by the region setting section on the display device based on the time applied to the medical information.

With this configuration, it may be possible to extract at least one event to be displayed on the display device from multiple pieces of medical information and display the at least one event extracted on the display device within the range of a set time region. With this configuration, it may be possible to display the at least one event to be paid attention to on the display device within the range of the time region to be paid attention to. It may be possible to check the process of the surgery.

Embodiments of the present disclosure will be described below with reference to the drawings.

First Embodiment

Figure 1:
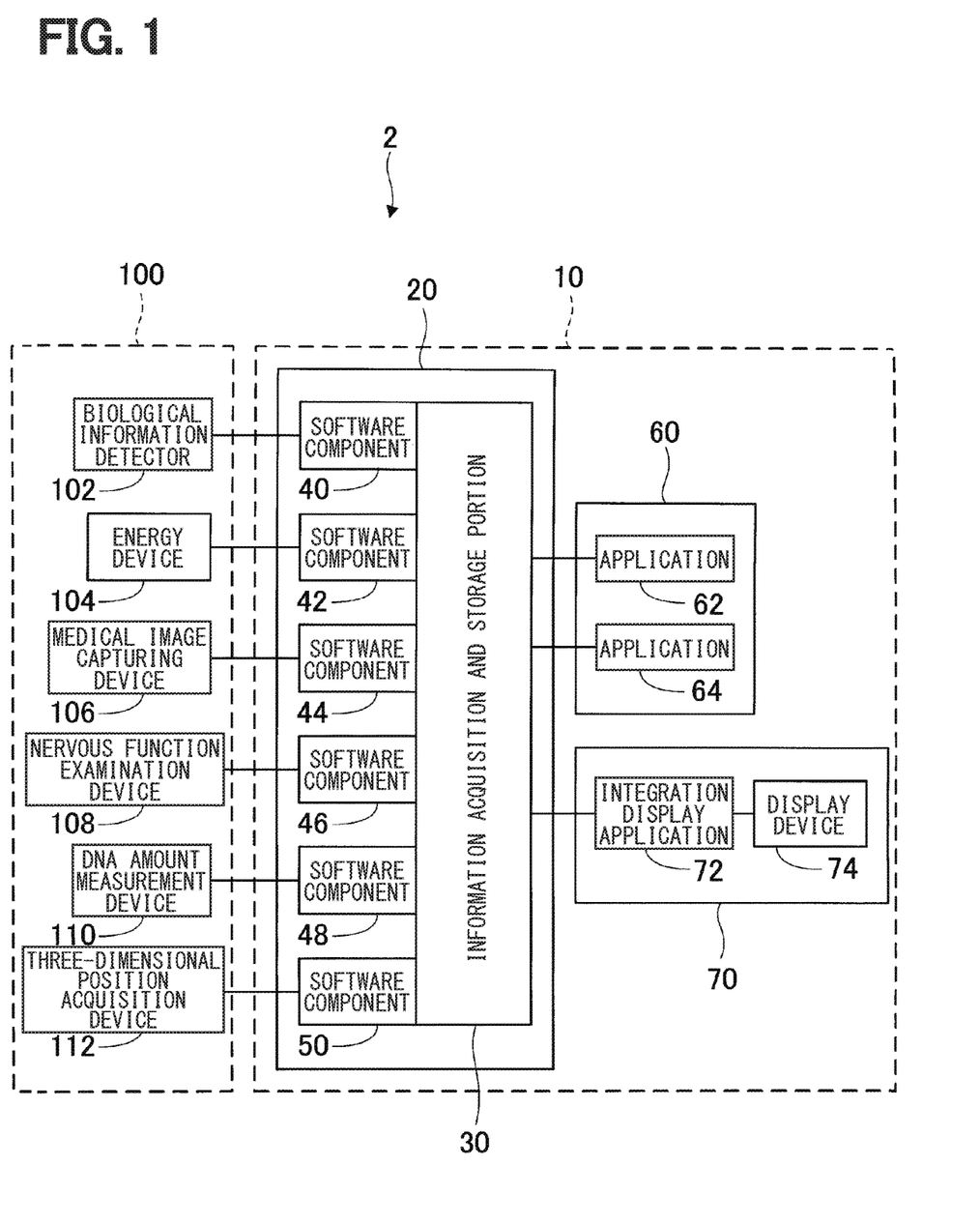
FIG. 1 is a block diagram illustrating a configuration of an information integrating apparatus according to a first embodiment.

An information integration system 2 illustrated in FIG. 1 includes an information integrating apparatus 10 and a medical device group 100. The medical device group 100 includes a biological information detector 102, an energy device 104, a medical image capturing device 106, a nervous function examination device 108, a DNA-amount measurement device 110, and a three-dimensional position acquisition device 112.

The information integrating apparatus 10 is used for integrating various medical information in an operating room, storing the integrated medical information, and displaying the integrated medical information. The information integrating apparatus 10 has known computers 20, 60, and 70 including a CPU, a RAM, a ROM, a HDD, and other components.

In the information integrating apparatus 10, the CPU in each of the computers 20, 60, and 70 executes a program installed in the HDD, so that information integration processing to be described later is performed. In view of function, the information integrating apparatus 10 includes an information acquisition and storage portion 30, software components 40 to 50 (i.e., 40, 42, 44, 46, 48, 50), applications 62 and 64, an integration display application 72, and a display device 74.

The information acquisition and storage portion 30 and the software components 40 to 50 are implemented by the computer 20. The applications 62 and 64 are implemented by the computer 60. The integration display application 72 and the display device 74 are implemented by the computer 70. For example, ORiN is used as the information acquisition and storage portion 30. ORiN is an abbreviation for Open Resource interface for the Network.

The information acquisition and storage portion 30 and the software components 40 to 50 function as interfaces for the information integrating apparatus 10 to transmit and receive information to and from the medical device group 100, regardless of the types of a programming language and a communication protocol. The software components 40 to 50 enable data to be passed between the information acquisition and storage portion 30 and the medical device group 100.

The information acquisition and storage portion 30 stores images, biological information, and other information in a HDD or other components as medical information acquired through communication with the medical device group 100.

The information acquisition and storage portion 30 applies a label that specifies medical information and a time when medical information is acquired to medical information acquired every predetermined time interval, and stores the medical information in a HDD or other components. The time applied to the medical information is acquired from a clock (not shown) included in the information integrating apparatus 10 and is managed on a unified time axis.

The applications 62 and 64 uses the medical information passed between the information acquisition and storage portion 30 and the medical device group 100 to output analysis results to files, display the analysis results as images, and edit the analysis results, as medical processes specific for the applications 62 and 64. The integration display application 72 integrates medical information stored in the information acquisition and storage portion 30 on the time axis and displays the medical information on the display device 74.

The display device 74 is, for example, a touch panel liquid crystal display, and is capable of displaying a three-dimensional image such as an MPR image and various operation buttons on a single screen. MPR is an abbreviation for Multi Planar Reconstruction. The display device 74 also outputs signals corresponding to an input operation performed by a user on an operation button displayed on a touch panel and an operation of a mouse performed by the user to the information acquisition and storage portion 30.

The biological information detector 102 detects a blood pressure, an electrocardiogram, oxygen saturation, a heart rate, a pulse wave, a brain wave, a myogenic potential, an anesthetic depth, and the like as biological information of a patient being operated.

The energy device 104 is a medical device that performs a surgery on an affected part of a patient such as an electric scalpel, a drill, and an ultrasonic irradiation device.

The medical image capturing device 106 is a device that captures the affected part of a patient, such as CT and MRI. CT is an abbreviation for Computed Tomography. MRI is an abbreviation for Magnetic Resonance Imaging.

The nervous function examination device 108 examines motor evoked potential and somatosensory evoked potential during a surgery. Hereinafter, the motor evoked potential is also referred to as MEP, whereas the somatosensory evoked potential is also referred to as SEP. MEP and SEP are also biological information.

The DNA-amount measurement device 110 performs a biopsy on tissue cut during a surgery and outputs an examination result whether the tissue is a cancer cell during the surgery.

The three-dimensional position acquisition device 112 acquires, as a medical device, a three-dimensional position of a surgical instrument such as an electric scalpel and forceps during a surgery. The method of acquiring the three-dimensional position of the surgical instrument is assumed as follows. For example, a marker is attached in advance to a specific position of the surgical instrument. A vector from a reference position set in advance in a space where the surgery is performed to the specific position of the surgical instrument is then specified as the three-dimensional position.

Next, information integration processing performed by the integration display application 72 in the information integrating apparatus 10 will be described. The flowchart of the information integration processing illustrated in FIG. 2 is performed when a power supply of the information integrating apparatus 10 is turned on and the start of the information integration processing is instructed by a switch or other devices.

Figure 2:
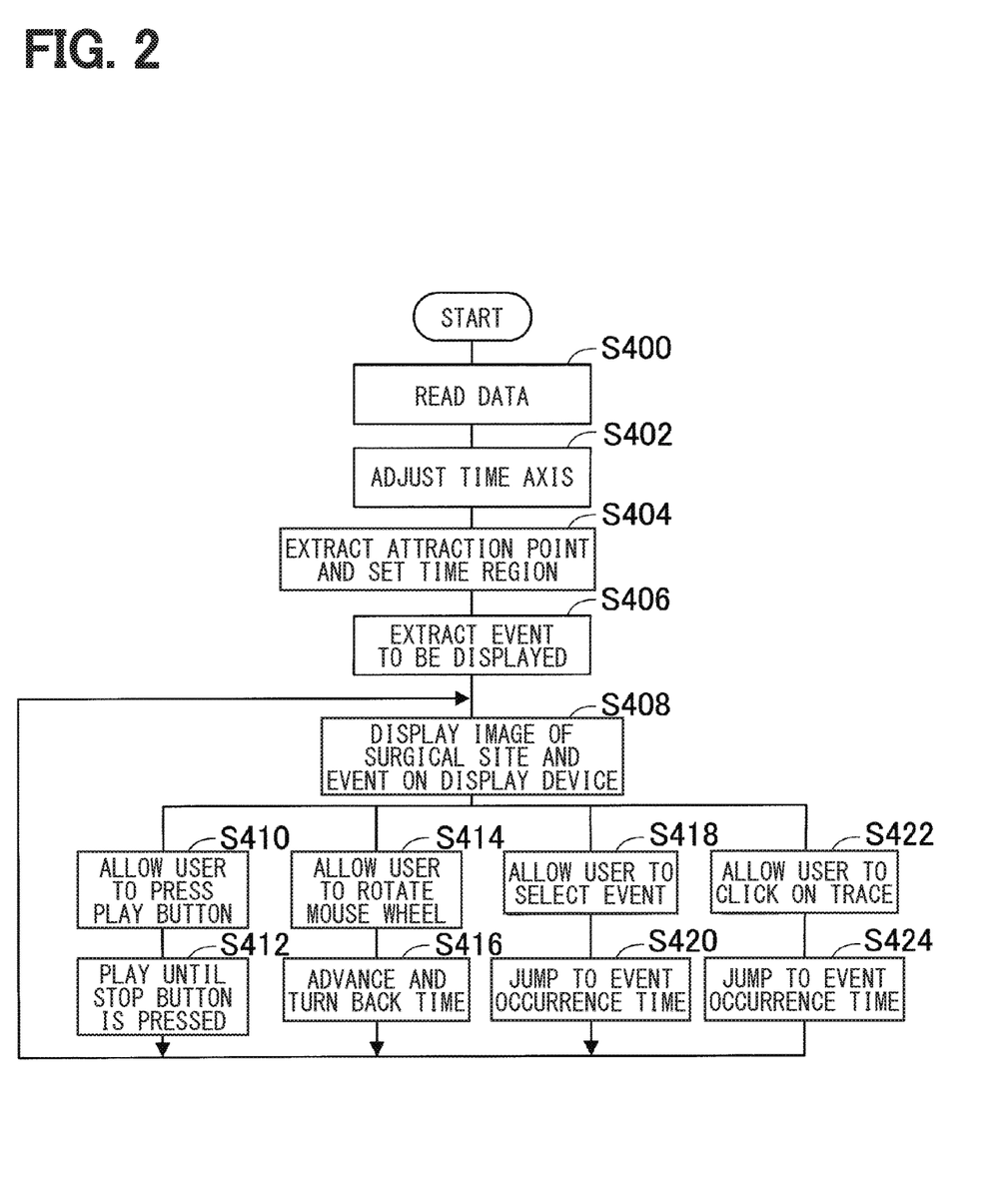
FIG. 2 is a flowchart illustrating information integration processing.
Figure 3:
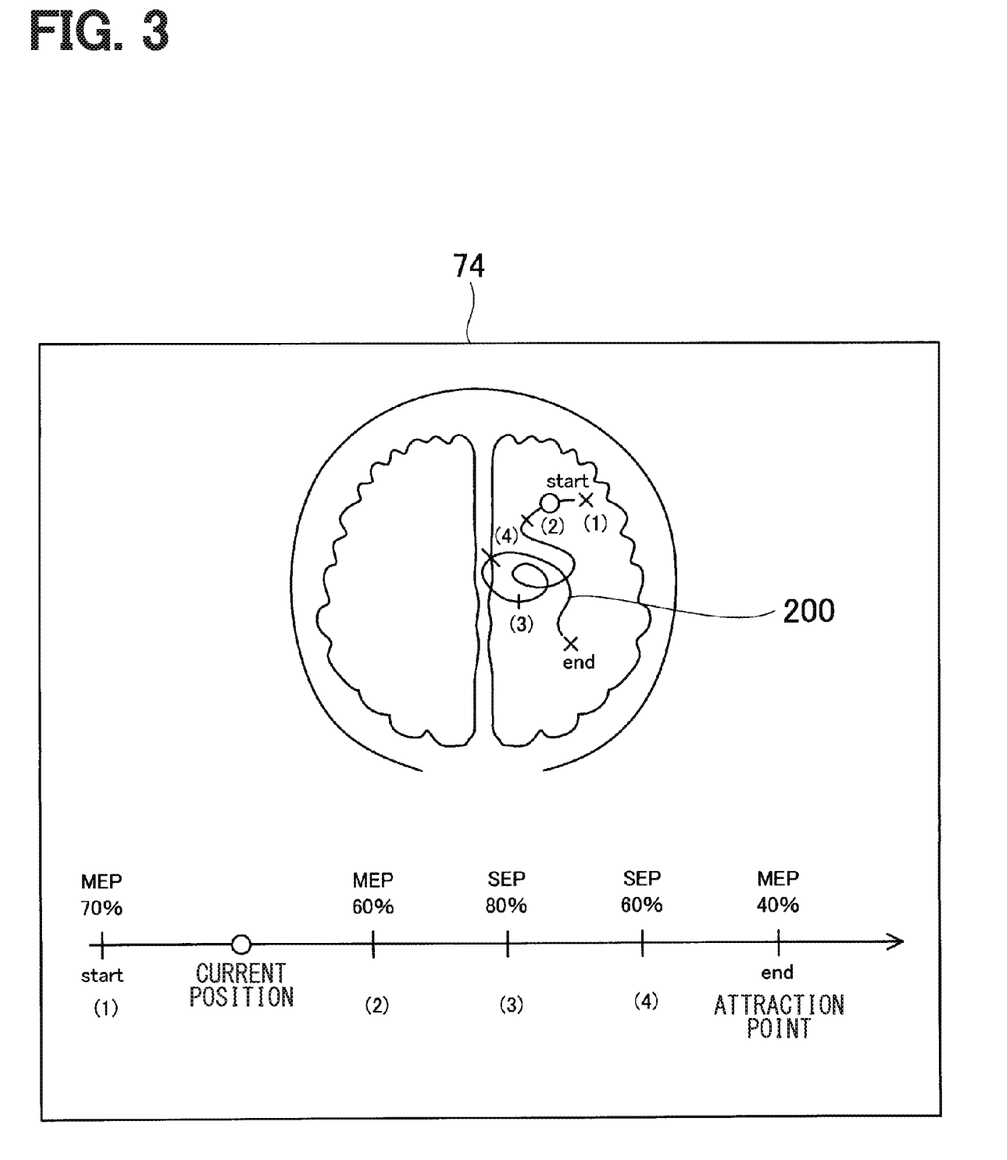
FIG. 3 is an explanatory view illustrating a display example of an electric scalpel trace.

FIG. 3 illustrates an MPR image captured when a surgery is performed on a brain using an electric scalpel as an example of an image displayed on the display device 74 by the information integration processing illustrated in FIG. 2. A CT image or an MRI image is used as the MPR image.

At S400, the integration display application 72 reads medical information that has been acquired from the medical device group 100 during a surgery and stored in the information acquisition and storage portion 30 from the information acquisition and storage portion 30.

At S402, the integration display application 72 adjusts the order of the medical information on a unified time axis based on a time applied to each piece of the medical information.

At S404, the integration display application 72 extracts an attraction point that is a reference time for setting a time region of at least one event to be displayed on the display device 74. The integration display application 72 sets a time period from a time when the surgery starts, which is prior to the attraction point, to the reference time that is the attraction point as the time region for displaying an image on the display device 74. When a user does not set the time region, the time region from when the surgery starts to when the surgery ends is set as a default value, for example.

For example, the user sets a condition that a MEP value is equal to or less than 40% as the condition for extracting an attraction point at S404. When the surgery is performed on a brain using an electric scalpel, the condition for extracting an attraction point may be set in advance by the integration display application 72. Alternatively, the user may set the condition for extracting an attraction point every time needed.

The time region for displaying an image and at least one event on the display device 74 using the attraction point as the reference time may be set in advance by the integration display application 72 using the time when the surgery starts as the start of the time region. Alternatively, the user may set the time region using the attraction point as the reference time every time needed. The attraction point does not have to be the end of the time region, and may be the start of the time region or may be a halfway point of the time region.

At S406, the integration display application 72 extracts at least one event that is to be displayed with the MPR image of the brain in the time region set at S404 on the display device 74.

At S408, the integration display application 72 displays the MPR image and at least one event extracted at S406 in the time region set at S404 on the display device 74. In the display example of FIG. 3, the attraction point is the time when the MEP value is less than or equal to 40%. As at least one event in the time region from the start of the surgery to the attraction point, an electric scalpel trace 200, the MEP value, and a SEP value are displayed with the MPR image on the display device 74. The electric scalpel trace 200, which is at least one event, is displayed to be superimposed on the MPR image.

Other than the electric scalpel trace 200, the MEP value, and the SEP value, biological information such as a brain wave and a pulse wave may be extracted from medical information as at least one event to be displayed on the display device 74 and be displayed.

There are multiple types of display layouts to be displayed on the display device 74. The integration display application 72 selects a display layout according to medical information to be displayed. Alternatively, the user sets a display layout.

Next, processes at S410 and S412, processes at S414 and S416, processes at S418 and S420, or processes at S422 and S424 are performed according to the user's operation. After the processes are performed, the processing returns to S408.

When the user presses a play button on a touch panel of the display device 74 at S410, the integration display application 72 plays at S412 the current position of the electric scalpel on the trace 200 and the MEP value and the SEP value at that position on the display device 74 until the user presses a stop button on the touch panel of the display device 74.

When the user rotates a mouse wheel at S414, the integration display application 72 plays at S416 the current position of the electric scalpel on the trace 200 and the position on the time axis with the MEP value and the SEP value at that time on the display device 74 while advancing or turning back the time according to the rotating direction of the mouse wheel.

When the user extracts an event at S418, the integration display application 72 displays at S420 an image at the time when the extracted event is generated on the display device 74.

When the user clicks the mouse on the trace 200 at S422, the integration display application 72 displays at S424 an image at the time on the trace 200 clicked by the user with the mouse on the display device 74.

It is possible to extract at least one event to be displayed on the display device 74 from medical information and display a change in the at least one event extracted on the display device 74 within the range of a set time region. This configuration enables the change in the at least one event to be paid attention to during a surgery to be displayed on the display device 74 within the range of the time region to be paid attention to. It is thus possible to check the process of the surgery.

In the first embodiment, the information integrating apparatus 10 corresponds to an information integrating apparatus, the information acquisition and storage portion 30 and the software components 40 to 50 correspond to an information acquisition portion, the information acquisition and storage portion 30 corresponds to an information storage portion, the integration display application 72 corresponds to an event extraction section, a region setting section, and a display section, and the display device 74 corresponds to a display device.

In addition, S404 correspond to the process performed by the region setting section, S406 corresponds to the process performed by the event extraction section, and S408, S412, S416, S420, and S424 correspond to the processes performed by the display section.

Second Embodiment

The configuration of an information integration system according to a second embodiment is substantially the same as that of the information integration system 2 according to the first embodiment except for a display example of an image displayed on the display device 74. The same reference signs are given to the same components as those of the first embodiment. Regarding the components with the same reference signs as in the first embodiment, the preceding description is referred to.

Figure 4:
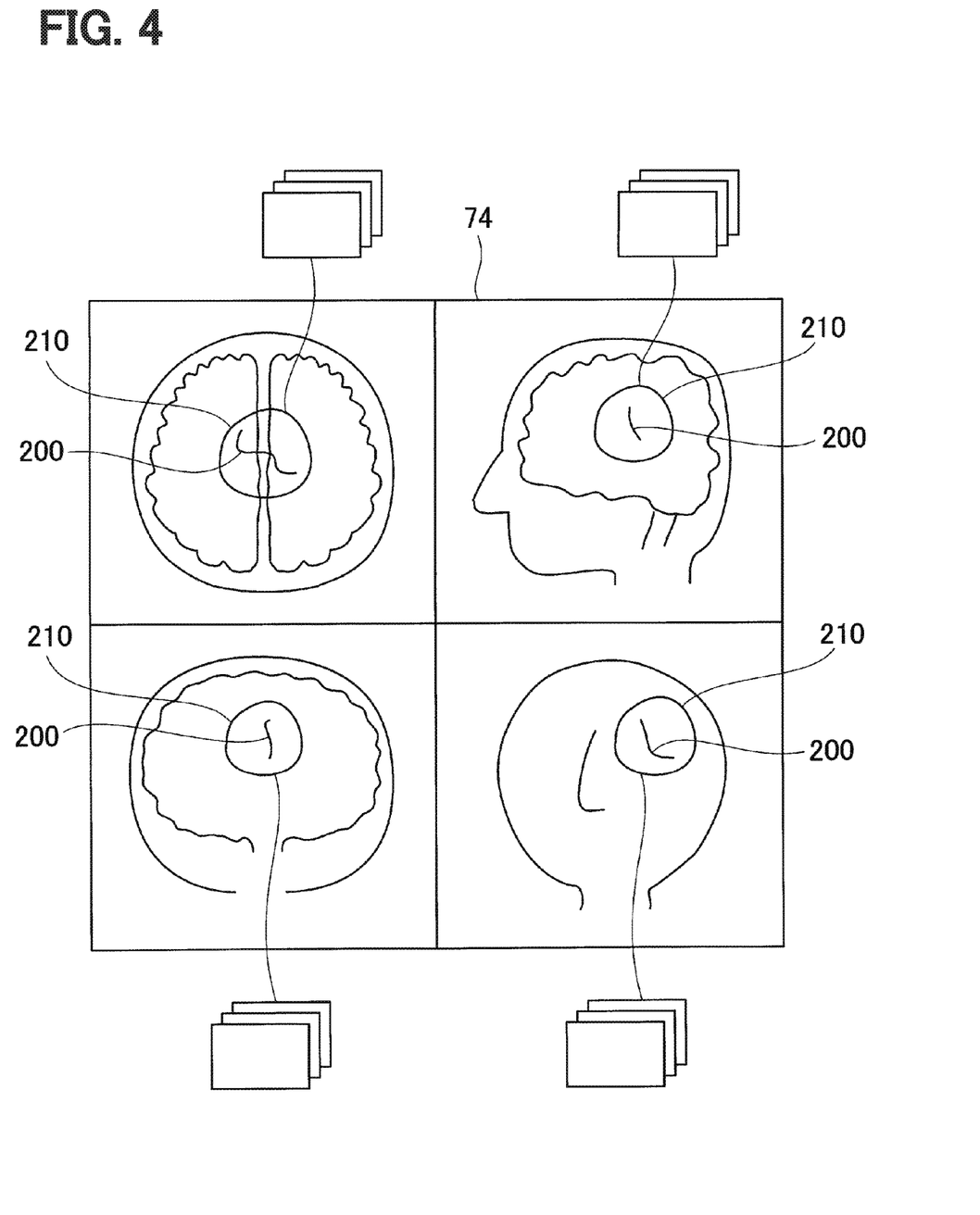
FIG. 4 is an explanatory view illustrating a display example according to a second embodiment.

As illustrated in FIG. 4, when a user specifies a space region 210 on any image of an axial section, a sagittal section, a coronal section, and a perspective image displayed on the display device 74 with a mouse or other devices, the integration display application 72 sets the corresponding space region 210 in other images. The time period from the start of a surgery to the end of the surgery is set as the time region, for example.

The integration display application 72 displays only at least one event generated in the space region 210 on the display device 74. In FIG. 4, the electric scalpel trace 200 in the space region 210 is displayed as the at least one event.

For example, when the user rotates a mouse wheel, only the image of the space region 210 is displayed on the display device 74, while the particular point of viewing the image does not change but the time is advanced or turned back according to the rotating direction of the mouse wheel.

According to the second embodiment, a time change in at least one event in the space region 210 to be paid attention to can be displayed on the display device 74 with the particular point of view. This configuration enables the process of a surgery to be checked based on the at least one event to be paid attention to and the space region 210.

The space region 210 corresponds to a space region in the second embodiment.

Third Embodiment

The configuration of an information integration system according to a third embodiment is substantially the same as that of the information integration system 2 according to the first embodiment except for a display example of an image displayed on the display device 74. The same reference signs are given to the same components as those of the first embodiment. Regarding the components with the same reference signs as in the first embodiment, the preceding description is referred to.

Figure 5:
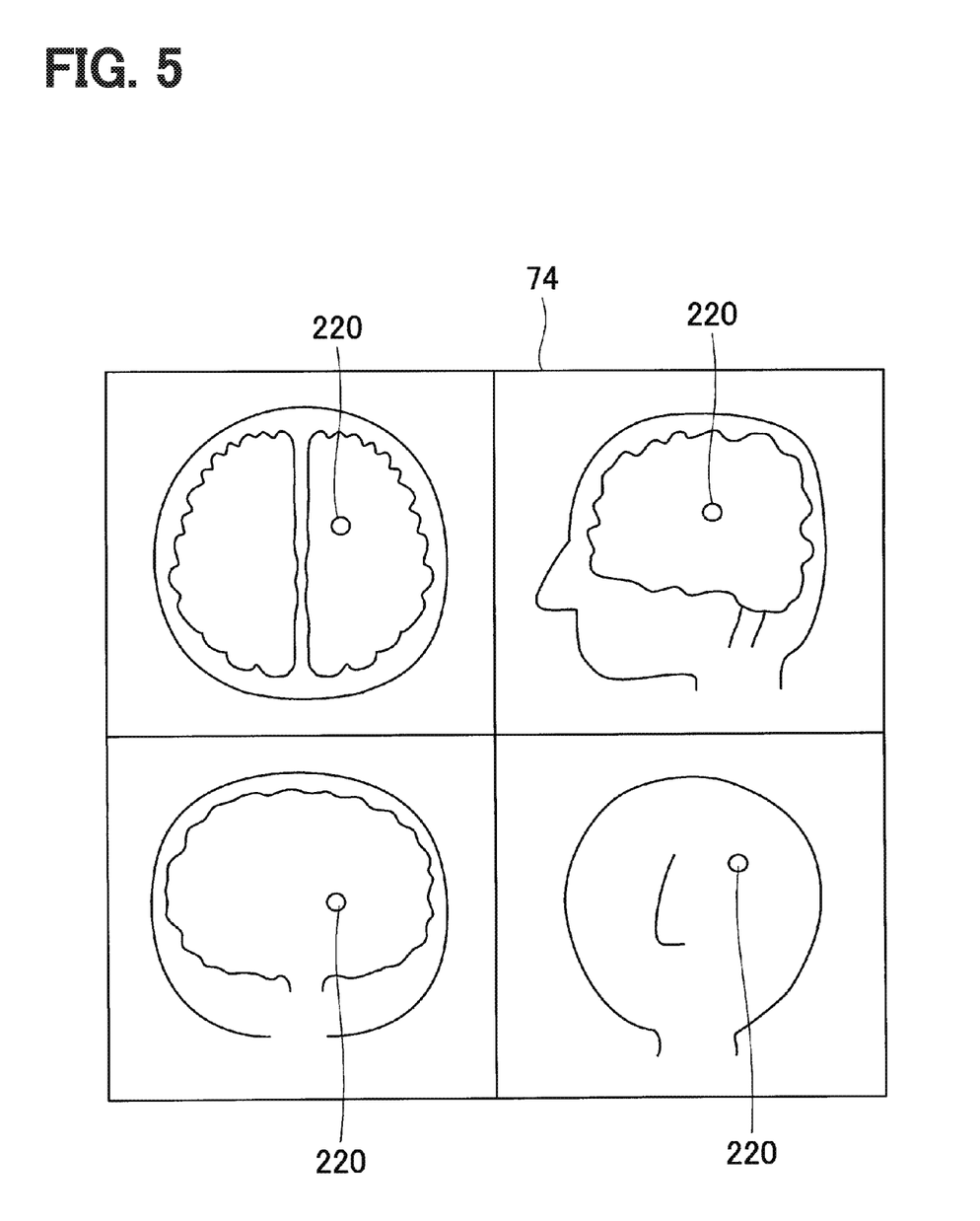
FIG. 5 is an explanatory view illustrating a display example according to a third embodiment.

As illustrated in FIG. 5, a user specifies a space region 220 on any image of an axial section, a sagittal section, a coronal section, and a perspective image displayed on the display device 74 with a mouse or other devices. When the space region 220 is specified in any of the images, the integration display application 72 sets the corresponding space region 220 in other images. The time period from the start of a surgery to the end of the surgery is set as the time region, for example.

In addition, the user sets the amount of heat or the temperature generated in the space region 220 by a surgical instrument such as an electric scalpel and a drill as at least one event.

For example, the space region 220 colored blue indicates less amount of heat generated, whereas the space region 220 colored red indicated more amount of heat generated. When the user rotates a mouse wheel to advance or turn back the time, the color of the space region 220 changes in a set time region. The amount of heat or the temperature is calculated by reflecting the operating state of the drill, reaction force applied to the drill, the material of the drill, and the cooling effect of cooling water in using the drill, for example.

Figure 6:
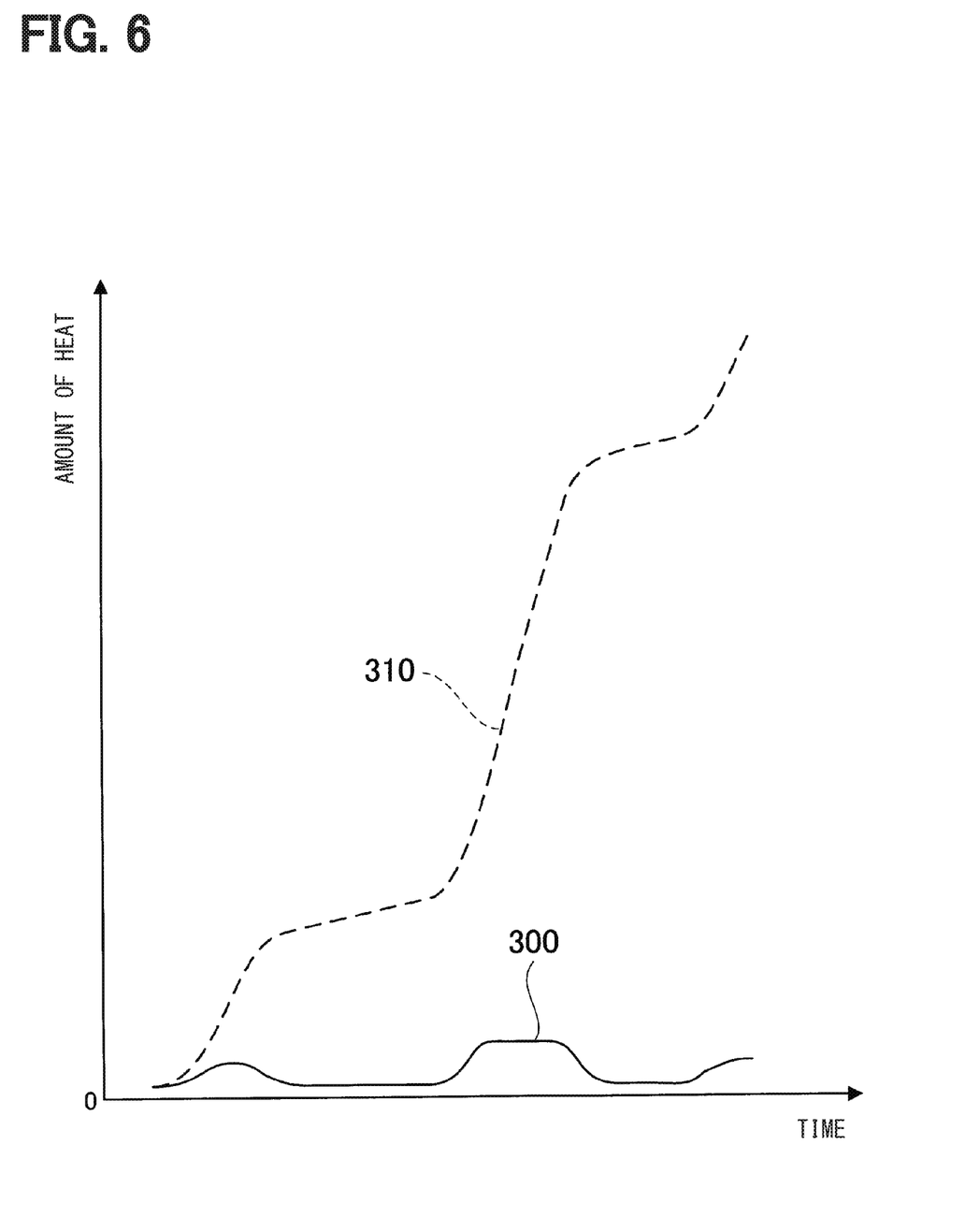
FIG. 6 is a characteristic diagram illustrating a change in the amount of heat at a surgical site.

As illustrated in FIG. 6, the amount of heat 300 instantaneously generated in the space region 220 over a time region and an accumulated value 310 of the amount of heat may be displayed on the display device 74.

According to the third embodiment, it is possible to easily check a change in the amount of heat in the space region 220 to be paid attention to on the display device 74 over a set time region.

The space region 220 corresponds to a space region in the third embodiment.

Other Embodiments

The time when an anesthetic is administered to a patient may be extracted as the attraction point for setting the reference time described above. Over a time region before and after the reference time when an anesthetic is administered to a patient, a time change in at least one event extracted may be displayed on the display device 74.

The information integrating apparatus 10 may check an abnormality cause occurred during a surgery, which is at least one event, based on multiple pieces of time-managed medical information stored in the information acquisition and storage portion 30.

The above embodiments have described the example of checking a surgery on the brain using the information integrating apparatus 10. The information integrating apparatus 10 may be used to check surgeries on the body parts that do not move during the surgery such as the teeth, bones, nose, and ears.

The information integrating apparatus 10 is constituted by two computers as described in the above embodiments. However, the number of computers is not limited to two and one computer or three or more computers may be used.

Multiple functions included in one component may be achieved by multiple components. Alternatively, one function included in one component may be achieved by multiple components. Multiple functions included in multiple components may be achieved by one component, or one function achieved by multiple components may be achieved by one component. The configurations of the above embodiments may be partially omitted. At least part of the configurations of the above embodiments may be added to or substituted by other parts of the configurations of the embodiments.

The present disclosure can also be achieved by, in addition to the information integrating apparatus described above, various modes such as an information integration system including the information integrating apparatus as a component, an information integration program that causes a computer to function as the information integrating apparatus, a recording medium having the information integration program recorded therein, and an information integration method.

It is noted that a flowchart or the processing of the flowchart in the present application includes multiple steps (also referred to as sections), each of which is represented, for instance, as S400. Further, each step can be divided into several sub-steps while several steps can be combined into a single step.

Control and method described in the present disclosure may be implemented by a special purpose computer created by configuring a memory and a processor programmed to execute one or more particular functions embodied in computer programs. Alternatively, the control units, the controllers and the methods described in the present disclosure may be implemented by a special purpose computer created by configuring a processor provided by one or more special purpose hardware logic circuits. Further alternatively, the control units, the controllers and the methods described in the present disclosure may be implemented by one or more special purpose computers created by configuring a combination of a memory and a processor programmed to execute one or more particular functions and a processor provided by one or more hardware logic circuits. The computer programs may be stored, as instructions being executed by a computer, in a tangible non-transitory computer-readable medium.

While various embodiments, configurations, and aspects of information integrating apparatus according to the present disclosure have been exemplified, the embodiments, configurations, and aspects of the present disclosure are not limited to those described above. For example, embodiments, configurations, and aspects obtained from an appropriate combination of technical elements disclosed in different embodiments, configurations, and aspects are also included within the scope of the embodiments, configurations, and aspects of the present disclosure.

What is claimed is:

1. An information integrating apparatus comprising:
a first processor and memory configured to:
acquire medical information from a plurality of medical devices used in a surgery;
manage a time when the medical information is acquired on an unified time axis to apply the time to the medical information; and
apply a label specifying the medical information to the medical information, and store the medical information in a storage device; and
a second processor and memory configured to:
extract an event to be displayed on a display device from the medical information stored in the storage device based on the label applied to the medical information;
set a time region for displaying the extracted event on the display device;
display, as the medical information, an image including a surgical site and the extracted event in the set time region set on the display device based on the time applied to the medical information;

set a space region to be paid attention to in the image including the surgical site;

extract the event to be displayed on the display device from the medical information generated in the set space region, the event being connected to the set space region;

display the event and the set space region on the display device; and select the space region in the image including the surgical site.

2. The information integrating apparatus according to claim 1, wherein:

the second processor and memory is configured to display a time change in the event in the time region as viewed from a particular point on the display device.

3. The information integrating apparatus according to claim 1, wherein:

the second processor and memory is configured to extract an amount of heat generated at a surgical site during a surgery as at least one of the event.

4. The information integrating apparatus according to claim 1, wherein:

the second processor and memory is configured to determine a time when a value of biological information, which is the medical information, falls within a predetermined range as a reference time in setting the time region.

5. An information integrating apparatus comprising:

a display device that displays medical information; and a CPU connected with a storage device that is configured to:

acquire the medical information from a plurality of medical devices;

manage a time when the medical information is acquired on an unified time axis to apply the time to the medical information;

apply a label specifying the medical information to the medical information;

store the medical information in the storage device;

extract an event to be displayed on a display device from the medical information stored in the storage device based on the label applied to the medical information;

set a time region for displaying the event extracted on the display device;

display, as the medical information, an image including a surgical site and the event extracted on the display device based on the time applied to the medical information;

set a space region to be paid attention to in the image including the surgical site;

extract the event to be displayed on the display device from the medical information generated in the set space region, the event being connected to the set space region;

display the event and the space region on the display device; and select the space region in the image including the surgical site.

6. The information integrating apparatus according to claim 1 wherein the event includes at least one of a motor evoked potential, a somatosensory evoked potential during a surgery, and an output of a DNA-amount measurement device.

7. The information integrating apparatus according to claim 5 wherein the event includes at least one of a motor evoked potential, a somatosensory evoked potential during a surgery, and an output of a DNA-amount measurement device.

* * * * *